(12) United States Patent
Zheng et al.

(10) Patent No.: US 8,172,742 B2
(45) Date of Patent: May 8, 2012

(54) MAGNETIC STIMULATION APPARATUS FOR CENTRAL NERVOUS SYSTEM, CIRCUIT AND USE THEREOF, AND METHOD OF USING THE APPARATUS

(75) Inventors: Yunfeng Zheng, Beijing (CN); Jiang Wang, Tianjin (CN); Lin Xu, Yunnan (CN)

(73) Assignee: Yunfeng Zheng, Beijing (CN)

( * ) Notice: Subject to any disclaimer, the term of this patent is extended or adjusted under 35 U.S.C. 154(b) by 1179 days.

(21) Appl. No.: 11/917,732

(22) PCT Filed: Jun. 12, 2006

(86) PCT No.: PCT/CN2006/001289
§ 371 (c)(1),
(2), (4) Date: Dec. 14, 2007

(87) PCT Pub. No.: WO2006/133636
PCT Pub. Date: Dec. 21, 2006

(65) Prior Publication Data
US 2008/0200749 A1    Aug. 21, 2008

(30) Foreign Application Priority Data
Jun. 15, 2005    (CN) .......................... 2005 1 0077042

(51) Int. Cl.
*A61N 1/00*    (2006.01)
(52) U.S. Cl. .......................................... 600/13
(58) Field of Classification Search ................ 600/9–15
See application file for complete search history.

(56) References Cited

U.S. PATENT DOCUMENTS

| | | | | |
|---|---|---|---|---|
| 4,940,453 | A | * | 7/1990 | Cadwell .......................... 600/13 |
| 5,061,234 | A | | 10/1991 | Chaney |
| 5,267,938 | A | * | 12/1993 | Konotchick ...................... 600/9 |
| 6,123,658 | A | | 9/2000 | Schweighofer et al. |
| 2004/0078056 | A1 | | 4/2004 | Zangen et al. |

FOREIGN PATENT DOCUMENTS

DE    102 42 542    4/2004
(Continued)

OTHER PUBLICATIONS

International Search Report issued for PCT/CN2006/001289; dated Sep. 14, 2006; 4 pages.
(Continued)

*Primary Examiner* — John Lacyk
(74) *Attorney, Agent, or Firm* — Fulbright & Jaworski L.L.P.

(57) ABSTRACT

A magnetic stimulation apparatus for central nervous system and circuit thereof, and use of the apparatus and method of using the apparatus are shown. Controlling circuit design and outputting wave form signal to a drive power supply circuit enables the drive power supply circuit to output current of corresponding wave form to coils, and by means of the design of the shape, number of turns, size, interval of the coils, generates within a certain region inside the coils a desired time-variant magnetic field which is then applied to the brain of an animal or a human being so that the central nervous system can receive a wide area synergy magnetic stimulation with a precise wave form, high frequency or a combination of a plurality of frequency components, thus achieving the treatment of nervous and psychiatric diseases or brain function improvement in combination with behavior guidance, thought guidance, or psychological guidance.

15 Claims, 4 Drawing Sheets

FOREIGN PATENT DOCUMENTS

| | | |
|---|---|---|
| JP | 53-53192 | 5/1978 |
| JP | 2000-510747 | 8/2000 |
| JP | 2001-526947 | 12/2001 |
| JP | 2002-524161 | 8/2002 |
| JP | 2004/511314 | 4/2004 |
| JP | 2005095591 | 4/2005 |
| JP | 08/280820 | 11/2008 |
| WO | WO97/40887 A1 | 11/1997 |
| WO | WO-00/02624 | 1/2000 |
| WO | WO-02/09811 | 2/2002 |
| WO | WO-02/085449 | 10/2002 |
| WO | WO-03/017061 | 2/2003 |

OTHER PUBLICATIONS

Office Action issued for South Korean Patent Application No. 10-2008-7000322, dated Jan. 29, 2010, 7 pages with the English translation.

Office Action issued for Japanese Patent Application No. 2008-516110, dated Jun. 29, 2010, 5 pages (with English translation).

The Extended European Search Report issued for EP06761298.6, dated May 24, 2011, 8 pages.

Notice of Allowance issued for Korean Patent Application No. 10-2008-7000322, dated Dec. 27, 2010, 4 pages (with English translation).

Xulin, et al. "Behavioral stress facilitates the induction of long-term depression in the hippocampus"; Nature (1997) 387: 497-500.

Rogan, M. et al., "Fear conditioning induces associative long-term potentiating in the amygdale", Nature (1997) 390: pp. 604-607.

Philips, R.G. et al., "Differential contribution of amygdale and hippocampus to cued and contextual fear conditioning". Behav. Neuroscience (1992) 12: pp. 854-863.

Falls, W.A., et al., "Extinction of fear-potentiated startle: blockade by infusion of an NMDA antagonist into the amygdale". Journal of Neuroscience, Mar. 1992, 12(3); pp. 854-863.

Li Shun-de, et al., "Effect of Amygdale lesion on the monoamine transmitters in rat brain", Medical Journal of national Defending Forces in Northwest China (2004), 25 (4):pp. 257-259.

Tang, Y.P., et al., "Genetic enhancement of learning and memory in mice", Nature (1999( 401: pp. 63-69.

Marsicano, G., et al., "The endogenous cannabinoid system controls extinction of advertise memories", Nature (2002) 418: pp. 530-534.

Han, J.S., "Acupuncture and endorphins", Neuroscience Letter (2004). 361 (1-3): 258-261.

Ji D, Sui., et al, "NMDA receptor in nucleus accumbens is implicated in morphine withdrawal in rats", Neurochemical Research (2004). 29 (11): pp. 2113-21120.

Han Ji-Sheng, "Induction of the release of central neuropeptides by peripheral electrical stimulation" J. Perking University, Health Science, (2004) 34: pp. 408-413.

Rusovan A., et al., "The stimulatory effect of magnetic field on regeneration of the rat sciatic nerve is frequency dependent", Experimental neurology (1992) 117; pp. 81-84.

Cordeiro P.G., et al., "Effect of a high-intensity static magnetic field on sciatic nerve regeneration in the rat", Plastic Reconstruction Surgery (1998); 83 (2); pp. 301-308. (1 page English Abstract submitted).

Longo F.M., et al., "Electromagnetic fields influence NGF activity and levels following sciatic nerve transection" Journal of Neuroscience, (1999). 55 (2); pp. 230-237.

Rusovan A., et al., "D600, aCa2+ antagonist, prevents stimulation of nerve regeneration by magnetic fields", Neuroreporteer (1992); Sep. 3, (9): pp. 813-814. (1 page English Abstract submitted).

Isobel J. Lever, et al., "Brain-Derived Neurotrophic Factor is released in a Dorsal Horn by Distinctive Patterns of Afferent Fiber Stimulation", The Journal of neuroscience (2001), 21 (12) pp. 4469-4477.

Rohan M., et al. "Low-field magnetic stimulation in bipolar depression using an MRI-based stimulator" Am J Psychiatry 2004, 161: pp. 93-98.

Carlezon W.A., et al., Antidepressant-like effects of cranial stimulation within a low-energy magnetic fields in rats Biol Psychiatry, 2005; 57: pp. 571-576.

* cited by examiner

MAGNETIC STIMULATION APPARATUS FOR CENTRAL NERVOUS SYSTEM, CIRCUIT AND USE THEREOF, AND METHOD OF USING THE APPARATUS

FIELD OF THE INVENTION

The present invention relates to a magnetic stimulation apparatus for central nervous system, a circuit thereof, use of the apparatus and method of using the apparatus.

BACKGROUND OF THE INVENTION

Central nervous system disease or psychiatric disease is considered as the capital killer in the 21st century since more and more people are suffering from such psychiatric disease as depression due to their growing life pace and stress. Epidemiologic survey has found that the prevalence, particularly lifetime prevalence, of schizophrenia and depression, is so high that the most heavily-suffered patients even commit suicide from time to time. After 1990s, survey on the special depression-hindered group indicates a usual per thousand prevalence of 10-20, whereas statistics published by the WHO in 2001 suggests that psychiatric disease in our country be responsible for 20% of the total burden levied by handicap plus illness, which is a percentage that crests the world and is still rising, and that produces such heavy social and economic burden that it is titled the greatest disabling disease (which deprives the patients of their ability to work and to live on their own all through their life). Psychiatric disease, which includes schizophrenia, depression, obsessive-compulsive disorder (OCD), attention deficit hyperactivity disorder (ADHD), post-traumatic stress disorder (PTSD), etc., belongs to a large family of chronic encephalopathy. Recently scientists include addictions to drugs, cyber-network and gambling, too, into psychiatric diseases. Among the above mentioned psychiatric diseases, the most devastating and one that levies the heaviest social and economic burden is depression, with a prevalence being 7-8% with respect to our country's total population and 20-50% to the aged population older than 60. Current treatment, apart from medical and psychological treatment, is primarily accomplished by electric stimulation or magnetic stimulation both belonging to physiotherapy, wherein the technology of magnetic stimulation, with transcranial magnetic stimulation (TMS) or repetitive TMS (rTMS) as its major development field, is now having its application scope expanded thanks to its characteristic of being analgesic, non-invasive and non-contacting compared with such side effects as pain, jerk, memory deficit (MD), etc., of the electric stimulation, as well as its other curative effects ever discovered during clinical treatment. However, it is difficult either for the current equipment to generate effective stimulation deep into the brain, or for cerebral cortex to receive ultra intensive stimulation which is converted into an effective stimulation deep into the brain due to the exponential attenuation of the magnetic induction with respect to distance. Although technology such as disclosed in patent 96180330.4, etc. is expected to meet the requirement of focusing the magnetic stimulation in the deep, it is difficult to generate a magnetic field with high energy while achieving a high frequency simultaneously as rTMS at present works at a frequency of 25 Hz at the most. Moreover, current magnetic stimulation apparatus frequently applied in biomedical field usually adopts one or more round shaped coils which are disposed in a plain and which, when used, is placed on the position to be stimulated and is used one-sidedly, thereby limiting the research orientation to the focusing of the magnetic stimulation and its electrophysiological sense thus introduced.

SUMMARY OF THE INVENTION

The present invention is to overcome the deficiency of the focusing magnetic stimulation by providing a magnetic stimulation apparatus for central nervous system for performing magnetic stimulation on the entire brain, as well as its use in treating nervous and psychiatric diseases and improving brain function and a method of controlling the magnetic stimulation apparatus.

In order to achieve the above purpose, the present invention provides the following technical solution: a magnetic stimulation circuit for central nervous system, including: a control circuit, a drive power supply circuit and coils that are sequentially connected, wherein the drive power supply circuit includes a drive circuit, a detection circuit and a main circuit, both the drive circuit and the detection circuit are connected to the control circuit and the main circuit respectively, and the coils are connected to the main circuit.

The main circuit may include a converting circuit for controlling currents in the coils to flow in the same or opposite direction.

The main circuit may include at least one insulated gate bipolar transistor (IGBT) and the control circuit generates a PWM signal which is used by the drive circuit to drive the insulated gate bipolar transistor in the main circuit to output a time-variant current to the coils which then generate a desired time-variant magnetic field.

The insulated gate bipolar transistor may be replaced by other fill-controlled power semiconductor devices, and the drive circuit is subject to corresponding modifications according to technical features of the replacement devices.

The control circuit may include a Digital Signal Processing (DSP) chip functioning as a main control chip, the drive circuit includes an optical coupler which is adapted to transfer a control signal sent from the control circuit to the main circuit, and the control circuit controls the drive circuit and the main circuit for the coils to generate a desired magnetic field, and the converting circuit may include at least one relay.

Furthermore, the present invention provides a magnetic stimulation apparatus for central nervous system, including a magnetic stimulation circuit, wherein the magnetic stimulation circuit includes a control circuit, a drive power supply circuit and coils that are sequentially connected, the drive power supply circuit includes a drive circuit, a detection circuit and a main circuit, both the drive circuit and the detection circuit are connected to the control circuit and the main circuit respectively, and the coils are connected to the main circuit.

The coils include at least a coaxial, parallel, and symmetrically disposed identical coil pair, with currents in the coil pair being synchronous in time and identical in intensity and the main circuit includes a converting circuit for controlling the currents in the coil pair to flow in the same or opposite direction.

The main circuit may include at least one insulated gate bipolar transistor (IGBT) and the control circuit generates a PWM signal which is used by the drive circuit to drive the insulated gate bipolar transistor in the main circuit to output a time-variant current to the coils which then generate a desired time-variant magnetic field.

The insulated gate bipolar transistor may be replaced by other full-controlled power semiconductor devices, and the drive circuit is subject to corresponding modifications according to technical features of the replacement devices.

The control circuit may include a DSP chip functioning as a main control chip, the drive circuit includes an optical coupler which is adapted to transfer a control signal sent from the control circuit to the main circuit, and the control circuit controls the drive circuit and the main circuit for the coils to generate a desired magnetic field, and the converting circuit may include at least one relay.

Still further, the present invention provides use of a magnetic stimulation apparatus for central nervous system, which involves treating central nervous system disease or psychiatric disease or improving brain function through selecting a time-variant magnetic field having appropriate parameters to stimulate entire brain of an animal or a human being.

The appropriate parameters include at least parameters of wave form, frequency and peak value intensity of current relating to the coil in the apparatus, and wave form, frequency and peak value intensity of corresponding induced magnetic field.

The appropriate parameters further include intra-train frequency and inter-train frequency in the case of pulse train magnetic stimulation.

Curative effect of the treatment of central nervous system disease or psychiatric disease is improved by introducing behavior guidance, thought guidance, or psychological guidance prior to, in the middle of, or after the magnetic stimulation, the specific procedure of which includes the following processes: magnetic stimulation having appropriate parameters is applied to the entire brain for an appropriate period, and in the middle of or after the magnetic stimulation, behavior guidance or thought guidance or psychological guidance is performed on those who are receiving or those who have received the magnetic stimulation.

Optionally, those who are to receive magnetic stimulation are subject to behavior guidance, thought guidance, or psychological guidance prior to the magnetic stimulation, magnetic stimulation having appropriate parameters is then applied to the entire brain for an appropriate period, and after the magnetic stimulation, those who have received the magnetic stimulation are subject to behavior guidance, thought guidance, or psychological guidance.

The disease includes depression, anxiety disorder, insomnia, chronic pain, post-traumatic stress disorder (PTSD), drug or alcohol dependence and addiction, psychic dependence on abnormal behavior, attention deficit, affective or mood disorder, schizophrenia, Parkinson's disease, neurodegenerative disease, dementia and nerve injury, etc.

The brain function includes learning and memory ability, cognitive ability, and anti psychological stress ability.

Even further, the present invention provides a method of controlling a magnetic stimulation apparatus for central nervous system with the apparatus being adapted to treat central nervous system disease or psychiatric disease or improving brain function, and the method involves electrifying coils through controlling magnetic stimulation circuit to apply a time-variant magnetic field to an objective region, wherein magnetic induction of the magnetic field has a gradient smaller than 100 Gs/cm, and the objective region has a scope matching head size of an animal or a human being.

The magnetic induction of the magnetic field may have a peak value smaller than 0.1 T.

During the process of the magnetic stimulation, the magnetic field is of one wave form or a combination of at least two wave forms, and the time-variant magnetic field is within a frequency range of 0.5 Hz to 2000 Hz.

As can be seen from the above technical solutions, the present invention, by controlling circuit design and outputting wave form signal to a drive power supply circuit, enables the drive power supply circuit to output current of corresponding wave form to coils, and by means of the design of the shape, number of turns, size, interval of the coils, generates within a certain region inside the coils a desired time-variant magnetic field which is then applied to the brain of an animal or a human being so that the central nervous system can receive a wide area synergy magnetic stimulation with a precise wave form, high frequency or a combination of a plurality of frequency components, thus achieving the treatment of nervous and psychiatric diseases or brain function improvement in combination with behavior guidance, thought guidance, or psychological guidance.

DETAILED DESCRIPTION OF THE EMBODIMENTS

A brief introduction of the related art is now given below for a better understanding of the technical content of the present invention:

Seen from the perspective of molecular biology, neurobiology and psychiatry, a wide area synergy magnetic stimulation having a precise wave form, modulated frequency (including high frequency) and a combination of a plurality of wave form/frequency components may possess such new senses as being capable of modulating the release of neurotransmitter and/or neuromodulator, modulating the receptor number and activity, activating the silent synapse, facilitating the long-term potentiation (LTP) of synaptic transmission, potentiating the synaptic plasticity, modulating the neuroendocrine. Moreover, the synergy or causal relations of the above effects, in combination with behavior guidance, thought guidance, or psychological guidance after the magnetic stimulation, results in a progress of the cognitive ability and the learning and memory ability, improvement of mental condition, treatment of nervous and psychiatric diseases. The reason is as follows:

The substance PCP that may cause schizophrenia-like symptom is found to be the excitatory amino acid receptor (NMDA receptor) antagonist, the relation of NMDAR with schizophrenia is attracting more and more attention. Kim (1980) was the first one to suggest that the dopamine (DA) release increase of schizophrenia is not primary, but may be the syndrome secondary to dysfunction of glutamatergic system. In the past 10 years, great progress has been made in the research on the NMDA receptor and transmitter function related with the pathogenesis of schizophrenia, particularly the research on the relation with such deficit symptom as negative symptom, cognitive symptom, which leads to the NMDA receptor dysfunction hypothesis on schizophrenia.

NMDA receptor, which is Magnesium-ion-blocked voltage-dependent excitatory amino acid transmitter gate-controlled calcium ion channel receptor, is activated under the partial depolarization condition of neuron membrane by means of cooperative effect of glutamate and glycin (usually functioning as inhibitory neurotransmitter) to result in the Calcium influx, thereby completing the entire process of depolarization of neuron and initiating successive cascade reaction. NMDA holds an important seat in the research of learning and memory cell related with molecular mechanism. In particular, LTP and the long-term depression (LTD) are considered as the inherent mechanism of synapse modification with the participation of NMHA receptor as its prerequisite.

Research by Xulin et al (1997) indicates that stress facilitates the hippocampus' LTD, while research by Michael T. Rogan et al (1997) indicates that stress leads to the facilitation of amygdala's LTP. In the hypothalamic-pituitary-adrenocortical (HPA) axis that is the main path controlling the emotional display, hippocampus and amygdala form a negative feedback. Research by Shuande LI Shuan-de et al (2004) indicates that the direction of neurotransmitter change is opposite to the psychotic change after the removal of amygdala, which gives us a hint that will the amygdala's LTP and/or hippocampus' LTD lead to the psychotic change of the neurotransmitter release?

Many psychiatric diseases are related more or less to such life events as stress, particularly the stressful experience during childhood or early ages, hence came out the quality-stress hypothesis. But why is the stressful experience during early or childhood ages? Suggested herein is a hypothesis that stressful experience of early ages forms an associative memory (conditioned) which is widely related with the environment, and the onset of diseases is the recall and intensification of the aversive memory. NR2A gradually replaces NR2B since the beginning of adolescence, a period associated with the general onset age of psychiatric diseases, which is not merely a coincidence. NR2B can produce stronger LTP than NR2A does and the replacement of NR2B by NR2A weakens hippocampus' LTD. If this replacement process in hippocampus and amygdala loses synchronicity or balance so that the replacement in hippocampus anticipates that in amygdala, the negative feedback inhibitory system will also lose balance, which leads to the onset of psychiatric diseases.

Research by Joe Z. Tsien et al (1999) indicates that NR2B may be called "smart gene" in that mice of NR2B over-expression in their research not only possess superior learning and memory ability, but also are faster in adapting to changes and exhibit better extinction of aversive memory (also referred to as re-learning ability). Recently, Giovianni Marsicano et al (2002) has found that endocannabinoid system is of key importance to the acceleration of the extinction of aversive memory, while gene mutant mice of insufficient receptor CB have much slower extinction of aversive memory than those of CB over-expression, and gene mutant mice of insufficient receptor CB with CB agonists added have their amygdala's LTP facilitated, LTD weakened or not generated. CB1 receptors, the natural ligand of which is still unknown, are of the greatest amount among the G protein-coupled receptor in brain.

Neuropeptide, particularly endogenous opioid peptide (EOP), has close relationship with emotion. Jisheng HAN et al studied the relationship between the electric stimulation with different frequencies and the release of neuropeptide (2004) and found out that the electric acupuncture increases the release of endogenous opioid peptide, and different frequency causes the release of different kinds of opioid peptide to increase, which means the release of neuropeptide is frequency dependent. They also found out (2004) that NMDAR agonist ketamine, if injected in nucleus accumbens, medicates the morphine withdrawal symptom. Jisheng HAN provided in 2002 a systematic description about the influence of electric stimulation to the release of neuropeptide.

Earlier research carried out by many people on the influence of magnetic stimulation to the nerve regeneration indicates that the effect of magnetic stimulation on the nerve regeneration is frequency dependent (RUSOVAN et al, 1992), while static magnetic stimulation, despite its high induction, has no effect (Cordeiro PG et al, 1989); that magnetic field stimulation on nerve helps to improve the activity and level of nerve growth factor (NGF) (Longo FM et al, 1999) whereas Calcium ion antagonist, MD600, prevents stimulation of nerve regeneration by magnetic fields (Rusovan A, Kanje M. 1992); and that the electrical nerve stimulation helps to release brain derived neurotrophic factor (BDNF) which is associated with the stimulation frequency/wave form combination and NMDA receptor, and it is the pulse wave form with high frequency and small interval (rectangular wave with a platform of 0.5 ms and the frequency of 100 Hz, and with 4 waves in a train each separated by an interval of 200 ms, adding up to 75 trains or 300 pulses), rather than the continuous lower frequency (1 Hz, 480 pulses) or higher frequency, fewer trains with wider intervals (100 Hz, and with 100 waves in a train each separated by an interval of 10s, adding up to 3 or 6 trains), that helps to release BDNF, which is inhibited by NMDA agonist D-AP-5 however (Isobel J. Lever et al, 2001). All these seem to suggest that there is a certain association among factors such as Calcium ion, NGF, BDNF, LTP (LTD), NMDA receptor, frequency of electric field and magnetic field, etc.

Rohan M et al (2004) occasionally found in the clinical research of psychiatric disease that a certain sequence in MRSI enhances the mood of bipolar-depression patients with considerable statistical sense, base on which the animal experiment also confirmed the effect as an antidepressant like by this magnetic stimulation (2005).

We found that, in the experiment of forced swimming (a learned helpless animal model usually used for screening or verifying the effects of anti-depressant), magnetic stimulation, in combination with behavior guidance thereafter (15 minutes for the open field), significantly improves the depressive-like behavior of model animals, while only behavior guidance or pure magnetic stimulation exhibits no perceptible effect.

We also found that, in fear-conditioning memory extinction experiment (after the foot shocks with acousto-optic (AO) prompt, conditioned reflex in response to the simple acousto-optic (AO) stimulation is recorded), different parameters may lead to different results, so as to strengthen or weaken the established fear conditioned reflex. Notice that certain stimulation may help to intervene the memory of negative events.

The above summary and analysis give us the following two points of teaching. First, the magnetic stimulation with a precise wave form and high frequency or a combination of a plurality of frequency components may function as a safe stimulation means for the NMDA receptor, and the magnetic stimulation with high frequency may, by means of NMDAR related LTP, bring profound changes to central nervous system in multiple aspects, and affect such process as the acquisition, extraction, modification, reinforcement of the memory to improve relearning ability, so as to treat some nervous and psychiatric diseases under certain conditions (such as behavior guidance after the magnetic stimulation); this inspires us to develop a wide area synergy magnetic stimulation apparatus suitable for clinical application which can generate a precise wave form, high frequency or a combination of a plurality of frequency/waveform components and which can overcome the deficiency of rTMS and electric stimulation, thus providing a new method for the treatment and prevention of nervous and psychiatric diseases. Second, the overall research carried out on the influence of magnetic stimulation having high frequency and a combination of a plurality of wave form/frequency components to many aspects such as LTP, learning and memory, neurotransmitter, extinction of memory, neuropeptide release, synaptic plasticity, etc., may bring fundamental impact to humankind in raising intelligence, preventing psychiatric diseases and even giving up drug addiction.

A detailed description of the present invention will be given with reference to the specific embodiments as follows.

Figure 1:
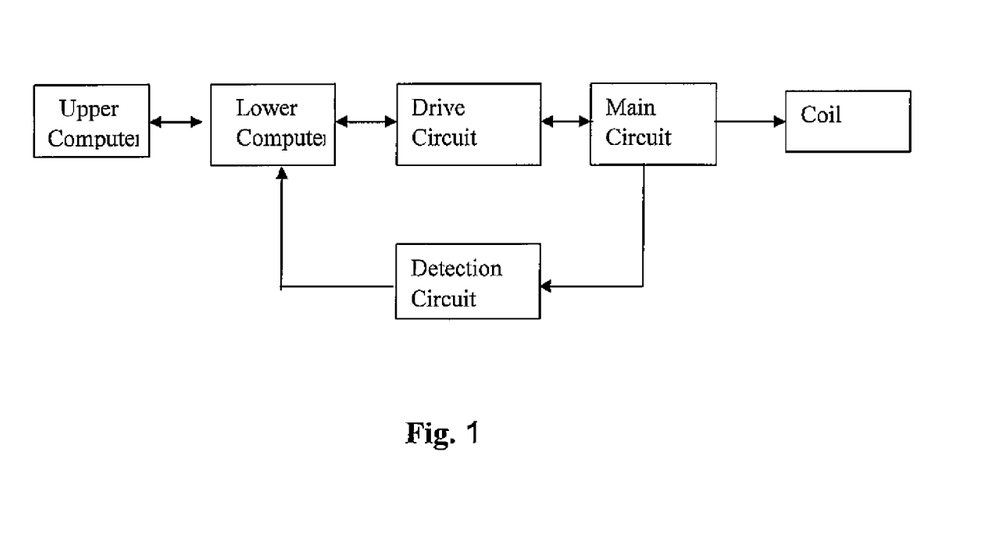
FIG. 1 is a circuit block diagram of the apparatus according to embodiment 1 of the present invention.

As shown in FIG. 1, the apparatus of the present invention includes a control circuit, a drive power supply circuit and coils, with the drive power supply circuit including a drive circuit, a detection circuit and a main circuit, the control circuit including an upper computer and a lower computer wherein the upper computer is a general PC or an industrial PC so as to operate in practical applications, and connects and communicates with the lower computer via RS232 interface to transmit command and parameters, and wherein the lower computer adopts a Digital Signal Processing (ASP) chip as the main control chip to receive the command and parameters from the upper computer, generate corresponding PWM signal which is then transferred to the drive circuit, while the drive circuit and the detection circuit are respectively connected to the lower computer and the main circuit, and the coils are connected to the main circuit, so that the control circuit generates a PWM signal, and the drive circuit drives the main circuit in which the insulated gate bipolar transistor (IGBT) outputs a time variant current to stimulate the coil pair and to stimulate and generate a time variant magnetic field. Meanwhile, the detection circuit samples the voltage and current values in the main circuit, monitors the work status of the main circuit in real time, and adjusts the output PWM signal if necessary, or cuts the coil circuit immediately in case of over current to prevent the damage of coil.

The drive circuit including an optical coupler is connected between the lower computer and the main circuit and primarily functions to shield the interference signal and drive the main circuit. (The above described part of circuit is not shown in the drawings.)

Figure 3:
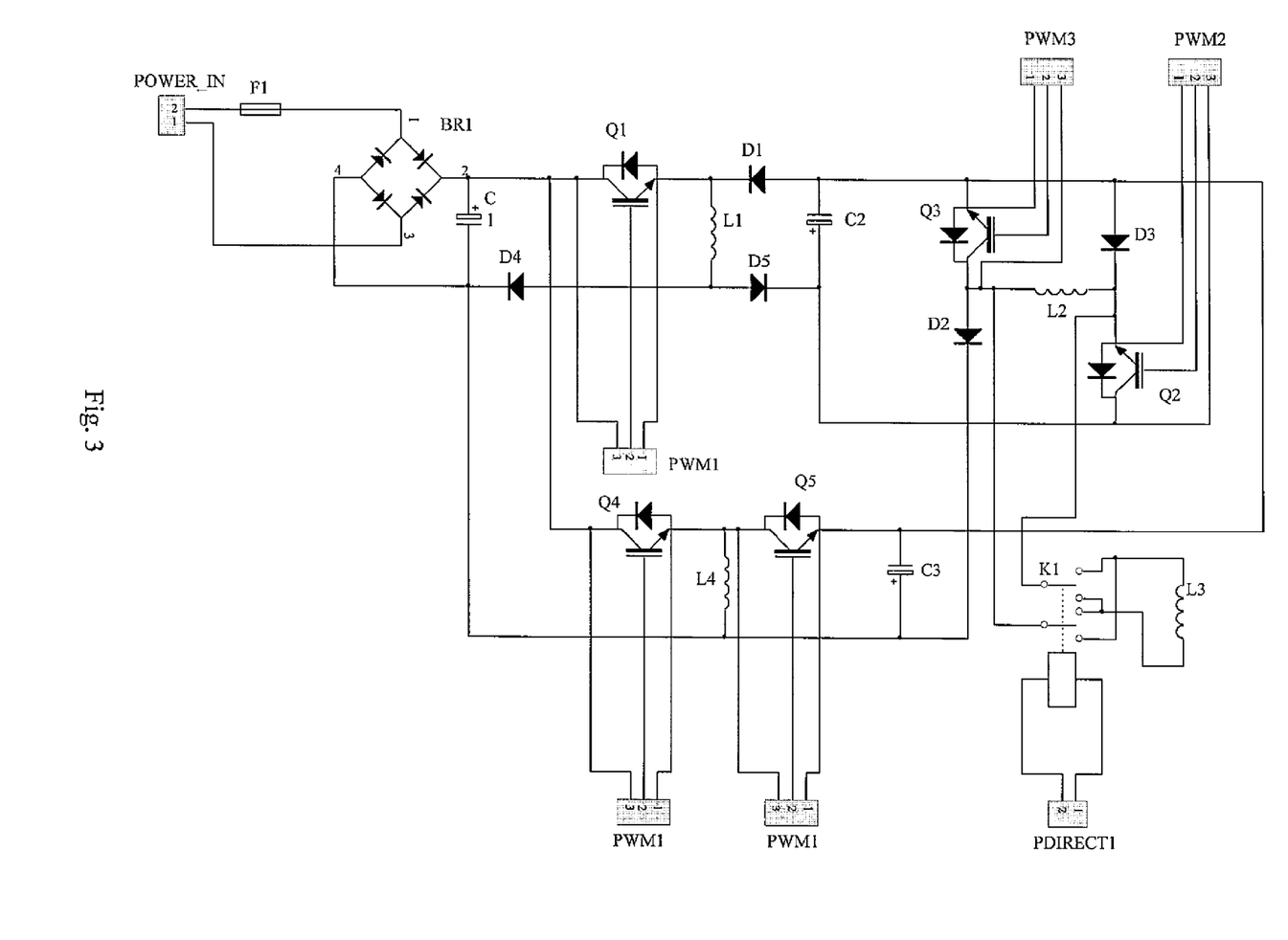
FIG. 3 is a diagram of the main circuit according to embodiment 1 of the present invention.

The main circuit, as shown in FIG. 3, includes a rectifier bridge BR1, five IGBTs Q1-Q5, and two electrolytic capacitors C2 and C3 with the electrolytic capacitors C2 and C3 being connected in parallel to the output terminals of the rectifier bridge BR1. The IGBT Q1, with its trigger terminal being connected to one pulse width modulation (PWM) terminal PWM1 of the drive circuit, is connected between the negative terminal of electrolytic capacitor C2 and the rectifier bridge BR1. The IGBTs Q4 and Q5, with their two trigger terminals connected to the other two PWM1 terminals of the drive circuit (the 3 PWM1 terminals are independent), are connected in series between the negative terminal of electrolytic capacitor C3 and the rectifier bridge BR1. The capacitors C2 and C3 are also connected in parallel to the terminals of the other two IGBTs Q2 and Q3, with the IGBTs Q2 and Q3 having their trigger terminals respectively connected to the other two PWM terminals PWM2 and PWM3 of the drive circuit. The coil L2 is connected between the emitter of the IGBT Q2 and the collector of the IGBT Q3. The converting circuit includes a relay DPDT K1 with the relay K1 having its two common terminals connected in parallel with both terminals of the coil L2, and its normally open terminal on one path connected to its normally closed terminal on the other path and its normally open terminal on the other path connected to its normally closed terminal on the former one path. The coil L3 is connected to the two connecting terminals and the coil of the relay K1 is connected to the two controlling terminals of the lower computer. The IGBTs may be discrete IGBT elements or an integrated IGBT module. The function of the optical coupler in the drive circuit may also be achieved by the IGBT module integrated with driving function.

The detection circuit adopts an LEM voltage sensor and a current sensor to detect the voltage between both terminals of capacitors C2 and C3 and the currents flowing through two coils L2 and L3, and applies filtering, amplification and A/D conversion to the detected signals, which are then transferred to the lower computer. (The above described part of circuit is not shown in the drawings.)

Figure 2:
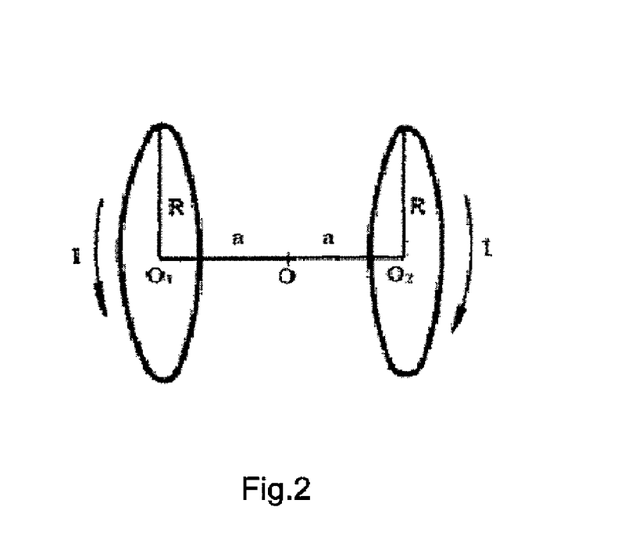
FIG. 2 is a diagram of the configuration of coils according to embodiment 1 of the present invention.

The coils are a coaxial, parallel, and symmetrically disposed identical coil pair, the structure of which is shown in FIG. 2 with the radius supposed as R and the distance being $2a=\sqrt{3}R$ to constitute a Maxwell coil pair and to generate a linear gradient magnetic field within the objective region between the two coils when the currents supplied flow in opposite direction but an approximately uniform magnetic field within the objective region when the currents supplied flow in the same direction. The objective region has a scope matching the head size of a human being. When the coils are supplied with the currents flowing in opposite direction, a linear gradient magnetic field is generated within a spherical region with its origin located at point O and its radius being 0.5a, into which the human head is located as much as possible. Additionally, the radius and the number of turns of the coil should be minimized as much as possible, so that the hardware of the drive power supply circuit can be less complicated and less power consumptive, which is easier to implement and makes the coil produce less heat to adapt to the high frequency current that generates high frequency magnetic field. An approximately uniform magnetic field can be obtained and the ergonomics requirement can be met by giving up a little linearity of the magnetic field gradient when setting R=180 mm, which is therefore applied in a preferred embodiment. In this case, if the coil is made to have 40 turns and the peak value of current in each turn is set to 5A, then a magnetic field gradient of 0.5 Gs/cm can be obtained in the central region. In practical application that sets the coil to have 40 turns and the peak value of current in each turn to be 40A, a magnetic field gradient may be up to 4 Gs/cm so as to achieve a satisfying curative effect. Besides, the lower computer may control the relay K1 to convert the coil L3 from its original connecting direction into a reverse direction so as to alter the direction of the coil current and switch the coil currents into a flowing in the same direction, thus generating even greater magnetic induction in the central region and improving the uniformity of magnetic field while reducing its gradient, which, in practical application, can lead to an effect which is different from that of the currents flowing in opposite direction.

While in operation, the user configures each parameter for system running by means of the upper computer and the parameter is transmitted to the lower computer via serial port. The lower computer, when receiving operating command, sends the PWM signal in the first place to control the Q1 and Q4 of the main circuit so that voltages on capacitors C2 and C3 reach the calculated desired values, and the voltages on capacitors C2 and C3 are acquired by the A/D converter of the lower computer via the detection circuit. When the voltages on capacitors C2 and C3 reach the desired values, the lower computer controls the on/off of Q2, Q3 by sending different PWM signals to them so as to generate various current wave forms, thus generating various corresponding time-variant magnetic fields. The main circuit control is divided into three phases, which are the rising phase, maintaining phase and dropping phase of the current. The rising phase of the current comes first, during which Q2, Q3 are both turned on and L2, L3 are subject to constant voltage (which is equal to the voltage on C2) so that their currents rise linearly with the slope that may be varied by changing the voltage on C2, and the maximum current in the coil may be varied by changing the time of this phase. Next comes the maintaining phase, during which Q3 is still on but Q2 switches on and off intermittently so as to maintain the current in L2, L3 in a substantially stable level. The final phase is the dropping phase, during which Q2, Q3 are both turned off, and the currents in L2, L3 have no choice but recharge the capacitor C3 via D2 and D3, which means that the coils L2, L3 have both of their terminals applied a reverse voltage equal to the voltage on C3, and the currents in the coils L2, L3 drop linearly until the values reduce to zero, with the slope that may be varied by changing the voltage on C3. After this dropping phase followed by a zero current interval, a new rising phase starts again, thus generating a cyclic time-variant current with a fixed period and precise wave form, and generating a periodical time-variant magnetic field with precise wave form.

Figure 4:
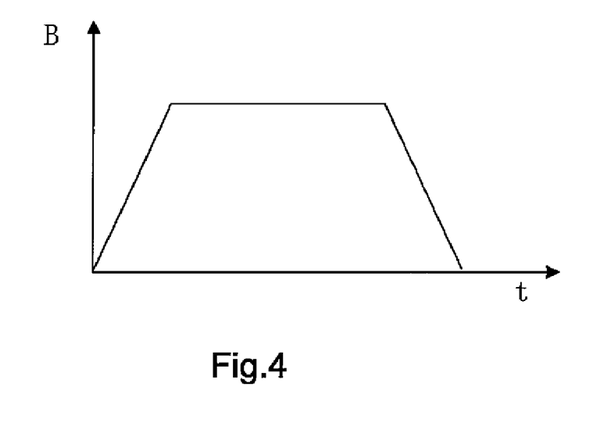
FIG. 4 is a wave form diagram adopted by embodiment 1 of the present invention.

When engaged in working, the control circuit is configured and controlled to generate the isosceles trapezium wave as shown in FIG. 4, which is then applied to the coil pair to generate the corresponding time-variant magnetic field and to induce, along the rising edge and falling edge of the isosceles trapezium wave, an electric field with positive and negative rectangular pulse waves within the objective region, thus meeting the medical requirement. In an example where a rising edge of 128 μs is succeeded by a platform of 768 μs, a falling edge of 128 μs and a zero-current platform of 768 μs which adds up to 1792 μs as the period (high frequency), the currents flow in opposite direction in the coil pair, and the peak value of current per turn is 20A (corresponding to a magnetic field gradient of 2 Gs/cm). It is also possible to implement a combination of a plurality of wave forms and frequency components and, by designing the number of periods for outputting and terminating the wave form, to constitute a train of magnetic stimulation which includes such parameters as the intra-train frequency and the inter-train frequency. For example, the above wave form is output for 10 periods then terminated for 27 periods, which constitute a train period, so that the pulses of the induced electric field have an intra-train frequency of 558 Hz approximately (or 1116 Hz approximately if ignoring the direction of the electric field) and an inter-train frequency of 15 Hz approximately (β rhythm); or, the same wave form may be terminated for 90 periods after being stimulated for 20 consecutive periods and have an inter-train frequency of 5 Hz (θ rhythm). By means of the upper computer, users may set different magnetic stimulation parameters in accordance with medical requirements. As the application for treating nervous or psychiatric diseases or improving brain function, the above magnetic stimulation may be applied to the whole brain of anyone in need of it (such as patients with depression) and kept continuously for a suitable period. As to continuous magnetic stimulation, an uninterrupted stimulation should not last too long each time to avoid the over activation of NMDA receptor and the possible side effect thus introduced, whereas trains of magnetic stimulation may last longer, such as 20 minutes. Trains of magnetic stimulation may be outputted intermittently such as for 2 seconds, for example, in every 10 seconds and be terminated in the other 8 seconds, thus being applied periodically. For those who are receiving or have received the magnetic stimulation, a behavior guidance, thought guidance, or psychological guidance is carried out to complete the entire process of the treatment or brain function improvement. For example, those who received the magnetic stimulation may experience or enter a novel environment, or they may be inspired to think through intelligence games or problem solving, wherein the problems may be embodied as a standard library and belong to the category of social science or natural science or knowledge of daily life. Combinations of the problems may be chosen in accordance with the educational background and intelligence quotient of patients, and be solved by those who received the magnetic stimulation. Alternatively, they may experience benign stimulation by means of specific music or image, or may keep their brains in a benign excitement by means of psychological assistance. The behavior guidance, thought guidance, and psychological guidance have such important feature as to give the patients more or less puzzle while enabling them to solve successfully.

Figure 5:
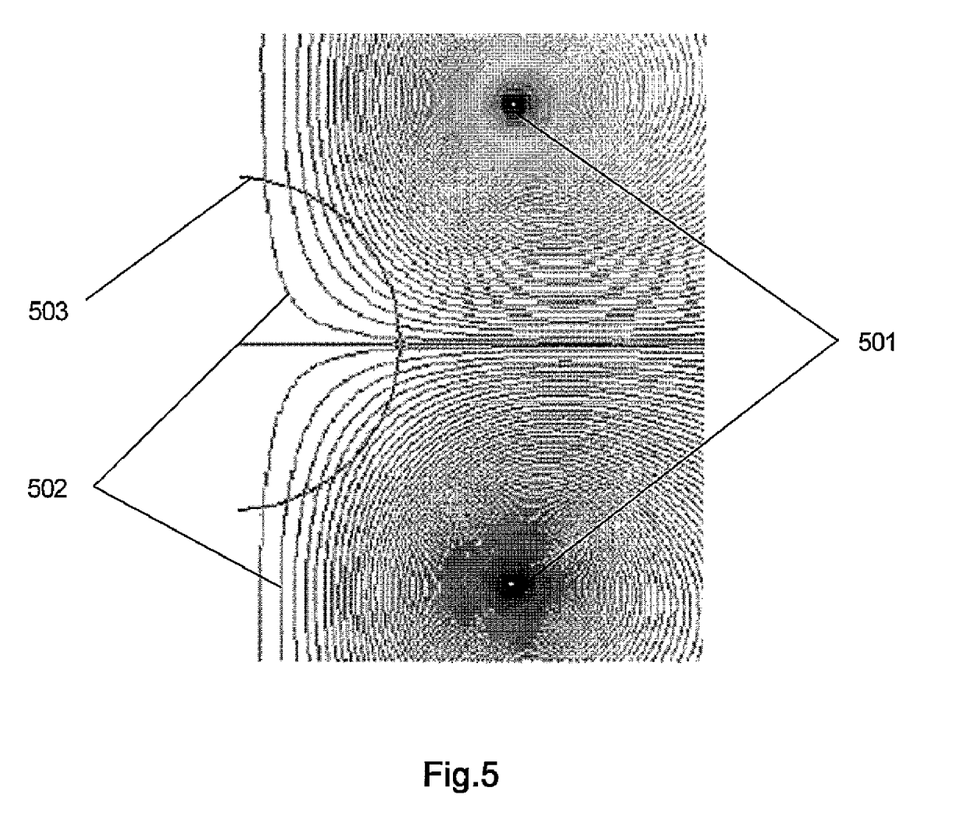
FIG. 5 is a diagram of the distribution of magnetic lines of force in the magnetic field that is generated through electrifying coils with the currents flowing in opposite direction.

FIG. 5 is a diagram of the distribution of magnetic lines of force in the magnetic field (only half is shown) which is generated through electrifying the coils with the currents flowing in opposite direction. As can be seen from the diagram, the magnetic lines of force within the objective region have linear gradient distribution, with 501 being the coils, 502 magnetic lines of force, and the region within 503 the objective region into which the human head is put during the process of treatment.

Figure 6:
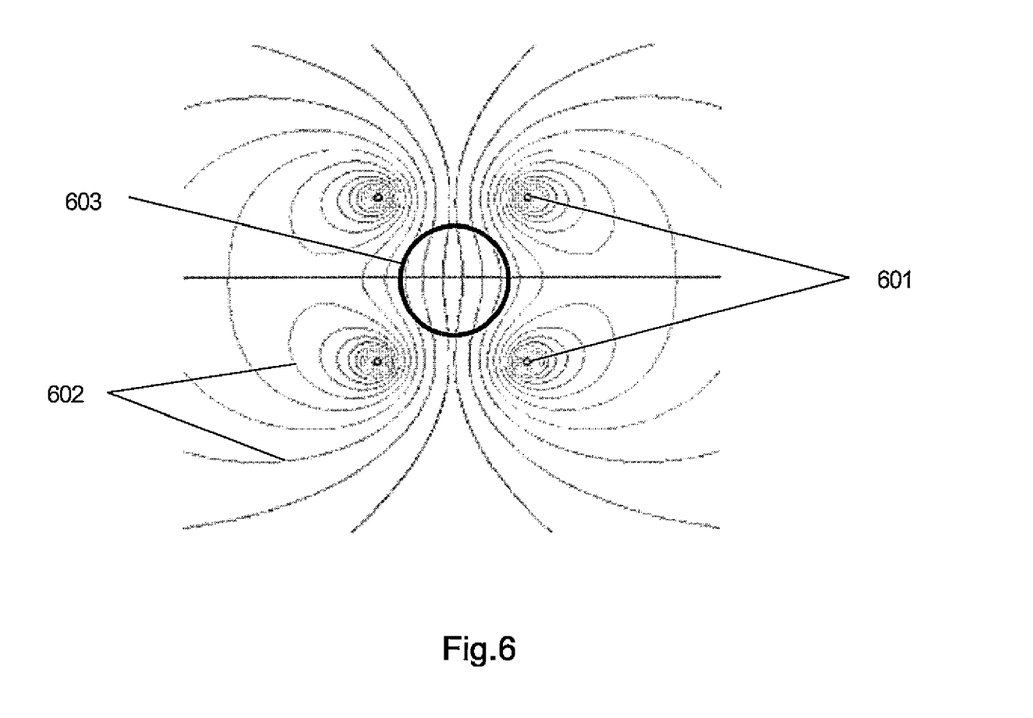
FIG. 6 is a diagram of the distribution of magnetic lines of force in the magnetic field that is generated through electrifying coils with the currents flowing in the same direction.

FIG. 6 is a diagram of the distribution of magnetic lines of force in the magnetic field that is generated through electrifying the coils with the currents flowing in the same direction. As can be seen from the diagram, the magnetic lines of force within the objective region have approximately uniform distribution, with 601 being the coils, 602 magnetic lines of force and 603 the objective region into which the human head is put during the process of treatment.

Figure 7:
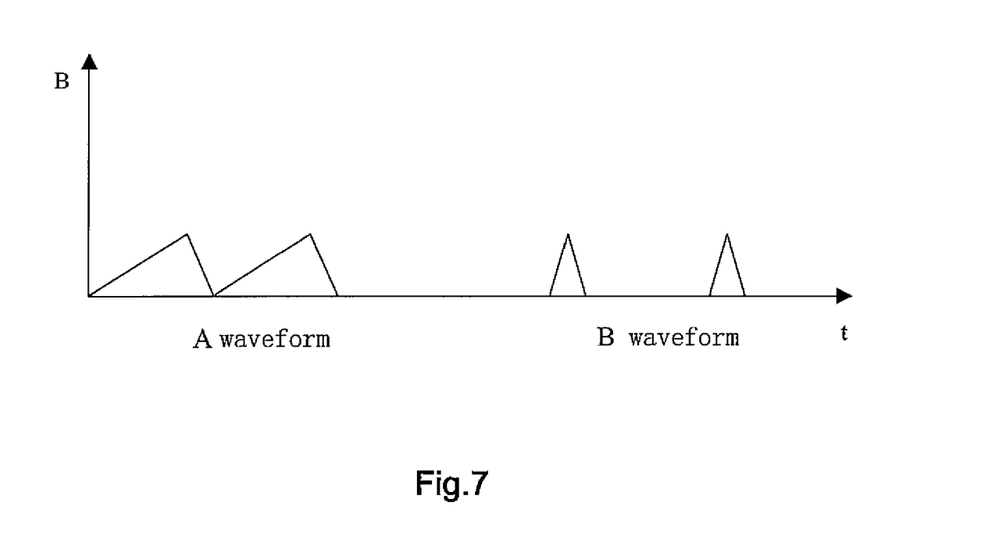
FIG. 7 is a wave form diagram adopted by embodiment 2 of the present invention.

In another embodiment 2 of the present invention which has a configuration identical to that of embodiment 1, combination of another two wave forms is generated through setting and controlling the control circuit, so that the coil pair generates corresponding magnetic field, as shown in FIG. 7 where wave A is a continuous sawtooth wave which has a frequency of 1000 Hz and lasts 3 minutes while wave B is an intermittent triangular wave which has a frequency of 2 Hz and lasts 3 minutes. These two waves occur by alternation for 3 cycles and last 18 minutes altogether to constitute a magnetic stimulation session, after which the above behavior guidance, thought guidance, or psychological guidance is carried out to complete the treatment of nervous and psychiatric diseases or brain function improvement.

As the use for treating nervous or psychiatric diseases or improving brain function, the method of using the apparatus may also include carrying out behavior guidance, thought guidance, or psychological guidance before the magnetic stimulation, wherein such guidance before the magnetic stimulation, which may differ from that after the magnetic stimulation, is aimed at extracting by means of the guidance the negative memory stored in the brain and exhibiting the same, whereas guidance after the magnetic stimulation is to modify, by means of "successful stress resistance", the negative memory and to reconstruct the negative feedback path of the hypothalamic-pituitary-adrenocortical (HPA) axis, or improve the antistress ability.

Apart from the above two preferred embodiments, the present invention may also adopt a coil with oval, rectangular shape or coil with other appropriate shapes including cubic shape, or the present invention may vary such coil parameters as the interval, number of turns, etc., or may alternatively adopt the combination of two or more coil pairs, or a coil with larger size, or a solenoid. The present invention may also, through controlling the control circuit and the drive circuit, achieve the combination of more wave forms, frequencies and amplitudes to complete a magnetic stimulation session. More wave forms of current including, for example, isosceles trapezium, may induce a magnetic field wave form including scalene trapezium, isosceles triangle, scalene triangle, etc. The output current may have a frequency lower than 1000 Hz. A magnetic stimulation session may be completed by the combination of a plurality of wave forms and a plurality of frequency components, or it is also possible to apply the currents flowing in opposite direction in case of high frequency, and currents flowing in the same direction in case of low frequency. Furthermore, the IGBTs in the main circuit may be replaced by other fall-controlled power semiconductor devices, such as the GRT, or power MOSFET or GTO, etc., and the main circuit is modified accordingly to adapt to the technical features of these devices, thus achieving the function of the main circuit. It is also possible to add into the main circuit two more IGBTs or other power semiconductor devices, as well as corresponding drive circuit and control circuit, so as to enable the currents in the coils to flow in both directions.

Detailed description has been made hereinabove to the magnetic stimulation method for central nervous system and its apparatus provided by the present invention in this specification, which explains the principle and embodiments of the present invention by means of specific examples. However, descriptions given to the above embodiments are merely meant to help understand the method and core spirit of the present invention, while those skilled in the art may make modifications to the embodiments and application scope according to the principle of the present invention. Therefore, content disclosed in this description should not be interpreted as limiting the present invention.

What is claimed is:

1. A magnetic stimulation circuit for central nervous system, comprising:
    a control circuit, a drive power supply circuit and coils that are sequentially connected, wherein the drive power supply circuit comprises a drive circuit, a main circuit, and a detection circuit for detecting the voltage and current values in the main circuit, both the drive circuit and the detection circuit are connected to the control circuit and the main circuit respectively, and the coils are connected to the main circuit,
    wherein the main circuit comprises at least one insulated gate bipolar transistor and the control circuit generates a PWM signal which is used by the drive circuit to drive the insulated gate bipolar transistor in the main circuit to output a time-variant current to the coils which then generate a desired time-variant magnetic field in an objective region, wherein the objective region is an entire brain, the magnetic induction of the time-variant magnetic field has a peak value smaller than 0.1 T, the magnetic induction of the time-variant magnetic field has a gradient smaller than 100 Gs/cm and the time-variant magnetic field comprises intra-train frequency and inter-train frequency.

2. The magnetic stimulation circuit for central nervous system of claim 1, wherein the main circuit comprises a converting circuit for controlling currents in the coils to flow in the same or opposite direction.

3. The magnetic stimulation circuit for central nervous system of claim 1, wherein the main circuit comprises at least one full-controlled power semiconductor device selected from a group consisting of a GRT, a power MOSFET and a GTO, and the control circuit generates a PWM signal which is used by the drive circuit to drive the full-controlled power semiconductor device in the main circuit to output a time-variant current to the coils which then generate a desired time-variant magnetic field.

4. The magnetic stimulation circuit for central nervous system of claim 2, wherein the control circuit comprises a Digital Signal Processing (DSP) chip functioning as a main control chip, the drive circuit comprises an optical coupler which is adapted to transfer a control signal sent from the control circuit to the main circuit, and the control circuit controls the drive circuit and the main circuit for the coils to generate a desired magnetic field, and the converting circuit comprises at least one relay.

5. An apparatus comprising
    a main circuit having at least one insulated gate bipolar transistor and a control circuit configured to generate a PWM signal which is used by a drive circuit to drive the insulated gate bipolar transistor in order to generate a desired time-variant magnetic field in an objective region, wherein magnetic induction of the time-variant magnetic field has a peak value smaller than 0.1 T, the magnetic induction of the time-variant magnetic field has a gradient smaller than 100 Gs/cm and the time-variant magnetic field comprises intra-train frequency and inter-train frequency.

6. The magnetic stimulation apparatus for central nervous system of claim 5, further comprising coils having at least a coaxial, parallel, and symmetrically disposed identical coil pair, wherein the apparatus is configured to provide currents to the coil pair that are synchronous in time and identical in intensity, and wherein the main circuit comprises a converting circuit for controlling the currents in the coil pair to flow in the same or opposite direction.

7. The magnetic stimulation apparatus for central nervous system of claim 5, wherein the main circuit comprises at least one full-controlled power semiconductor device selected from a group consisting of a GRT, a power MOSFET and a GTO, and the control circuit generates a PWM signal which is used by the drive circuit to drive the full-controlled power semiconductor device in the main circuit to output a time-variant current to generate a desired time-variant magnetic field.

8. The magnetic stimulation apparatus for central nervous system of claim 6, wherein the control circuit comprises a DSP chip functioning as a main control chip, the drive circuit comprises an optical coupler which is adapted to transfer a control signal sent from the control circuit to the main circuit, and the control circuit controls the drive circuit and the main circuit for the coils to generate a desired magnetic field, and the converting circuit comprises at least one relay.

9. A method for using a magnetic stimulation apparatus for central nervous system, said method comprising:
    setting appropriate parameters for stimulating the brain of a subject, wherein the appropriate parameters comprise intra-train frequency and inter-train frequency in the case of pulse train magnetic stimulation;
    generating a corresponding time-variant magnetic field according to the set appropriate parameters in an objective region, wherein the objective region is the brain of the subject, wherein the magnetic induction of the time-variant magnetic field has a peak value smaller than 0.1 T, and the magnetic induction of the time-variant magnetic field has a gradient smaller than 100 Gs/cm; and treating central nervous system disease or psychiatric disease or improving brain function using the generated corresponding time-variant magnetic field.

10. The use of a magnetic stimulation apparatus for central nervous system of claim 9, wherein the appropriate parameters comprise at least parameters of wave form, frequency and peak value intensity of current relating to the coil in the apparatus, and wave form, frequency and peak value intensity of corresponding induced magnetic field.

11. The use of a magnetic stimulation apparatus for central nervous system of claim 9, wherein the treatment of central nervous system disease or psychiatric disease provides improved curative effect by introducing behavior guidance, thought guidance, or psychological guidance prior to, in the middle of, or after the magnetic stimulation.

12. The use of a magnetic stimulation apparatus for central nervous system of claim 9, wherein magnetic stimulation having appropriate parameters is applied to the entire brain for an appropriate period, and in the middle of or after the magnetic stimulation, behavior guidance or thought guidance or psychological guidance is performed on those who are receiving or those who have received the magnetic stimulation.

13. The use of a magnetic stimulation apparatus for central nervous system of claim 9, wherein, those who are to receive magnetic stimulation are subject to behavior guidance, thought guidance, or psychological guidance prior to the magnetic stimulation, magnetic stimulation having appropriate parameters is then applied to the entire brain for an appropriate period, and after the magnetic stimulation, those who have received the magnetic stimulation are subject to behavior guidance, thought guidance, or psychological guidance.

14. The use of a magnetic stimulation apparatus for central nervous system of claim 9, wherein the disease is one of the following: depression, anxiety disorder, insomnia, chronic pain, post-traumatic stress disorder (PTSD), drug or alcohol dependence and addiction, psychic dependence on abnormal behavior, attention deficit, affective or mood disorder, schizophrenia, Parkinson's disease, neurodegenerative disease, dementia and nerve injury.

15. The use of a magnetic stimulation apparatus for central nervous system of claim 9, wherein the brain function is learning and memory ability, cognitive ability, or anti psychological stress ability.

\* \* \* \* \*